United States Patent [19]

Larkin et al.

[11] Patent Number: 5,507,733
[45] Date of Patent: Apr. 16, 1996

[54] SECURABLE COLLAR FOR FLUID CONNECTOR

[75] Inventors: Mark E. Larkin, Lindenhurst; David E. Kramer, Northbrook; Warren P. Frederick, Wonder Lake, all of Ill.

[73] Assignee: Abbott Laboratories, Abbott Park, Ill.

[21] Appl. No.: 353,048

[22] Filed: Dec. 9, 1994

Related U.S. Application Data

[63] Continuation-in-part of Ser. No. 129,233, Sep. 29, 1993, abandoned, which is a continuation-in-part of Ser. No. 36,005, Mar. 23, 1993, abandoned.

[51] Int. Cl.[6] .............................. A61M 25/00; F16L 21/06
[52] U.S. Cl. ........................... 604/283; 604/905; 285/322
[58] Field of Search ................................ 604/83, 86, 88, 604/107, 256, 283, 284, 905; 285/29, 27, 315, 322

[56] References Cited

U.S. PATENT DOCUMENTS

| | | | |
|---|---|---|---|
| 2,784,987 | 3/1957 | Corcoran | 285/82 |
| 3,394,950 | 7/1968 | Jenson | 285/35 |
| 3,413,021 | 11/1968 | Potts | 285/319 |
| 3,565,078 | 2/1971 | Vaillancourt | 604/256 |
| 4,103,941 | 8/1978 | Stoll | 285/238 |
| 4,323,065 | 4/1982 | Kling | 604/283 |
| 4,329,987 | 5/1982 | Rogers et al. | 604/283 |
| 4,405,163 | 9/1983 | Voges et al. | 285/305 |
| 4,723,948 | 2/1988 | Clark et al. | 604/283 |
| 4,895,570 | 1/1990 | Larkin | 604/411 |
| 4,950,254 | 8/1990 | Andersen et al. | 604/247 |
| 5,052,386 | 10/1991 | Fischer, Jr. | 128/207.15 |
| 5,120,324 | 6/1992 | Sancoff | 604/283 |
| 5,137,524 | 8/1992 | Lynn et al. | 604/283 |
| 5,197,895 | 3/1993 | Stupecky | 439/194 |
| 5,242,431 | 9/1993 | Kristiansen | 604/283 |
| 5,248,306 | 9/1993 | Clark et al. | 604/283 |
| 5,273,533 | 12/1993 | Bonaldo | 604/83 |
| 5,281,206 | 1/1994 | Lopez | 604/283 |
| 5,312,377 | 5/1994 | Dalton | 604/283 |

Primary Examiner—John D. Yasko
Assistant Examiner—Adam J. Cermak
Attorney, Agent, or Firm—A. Nicholas Trausch

[57] ABSTRACT

A securable collar is used with two connectors to prevent the inadvertent disconnection of IV tubing sets. The securable collar includes a housing supported by one of the connectors, a radial flange extending from the housing, a collar having a frustum-shape, two notches that separate the collar into two longitudinal segments, a transition portion on the exterior of the collar, and a sliding annular locking ring. The locking ring slides on the collar from a small diameter portion over the transition portion to a larger diameter portion. The annular locking ring compresses the larger diameter portion to pivot the longitudinal segments radially inward at the radial flange to grip the second connector.

15 Claims, 6 Drawing Sheets

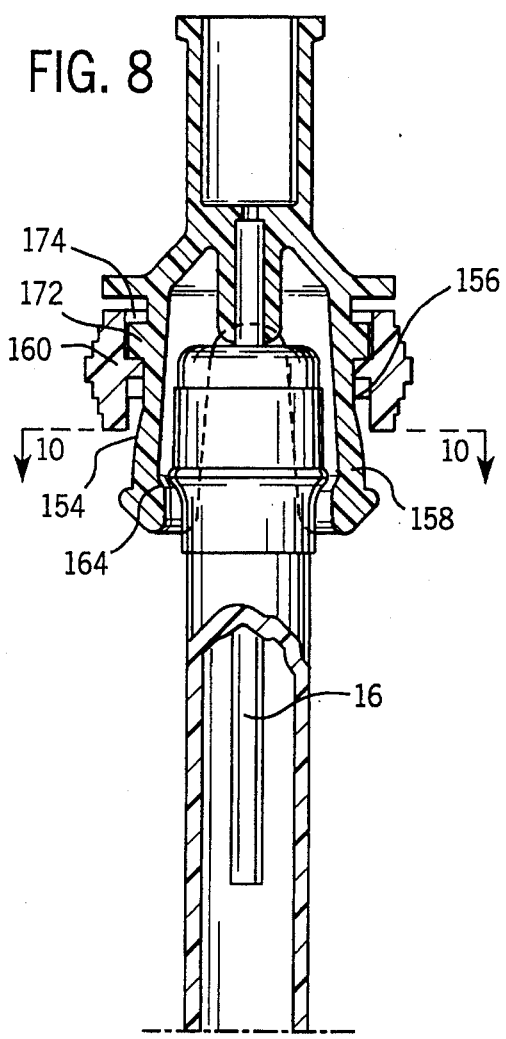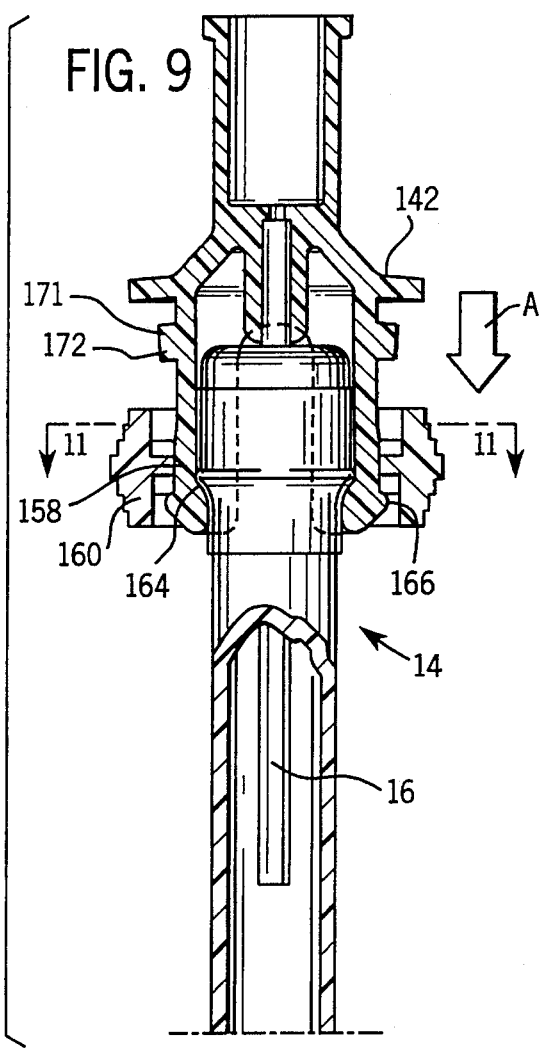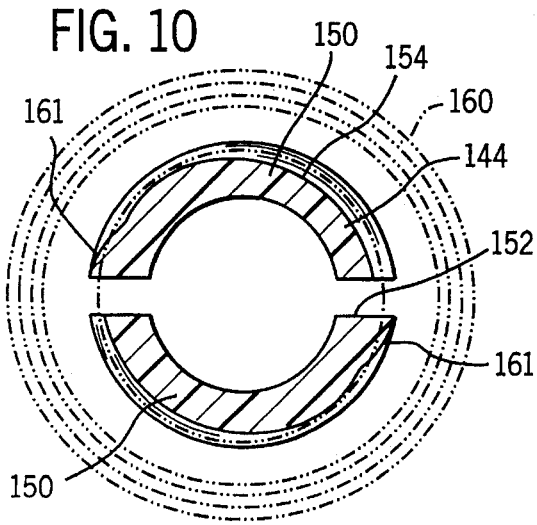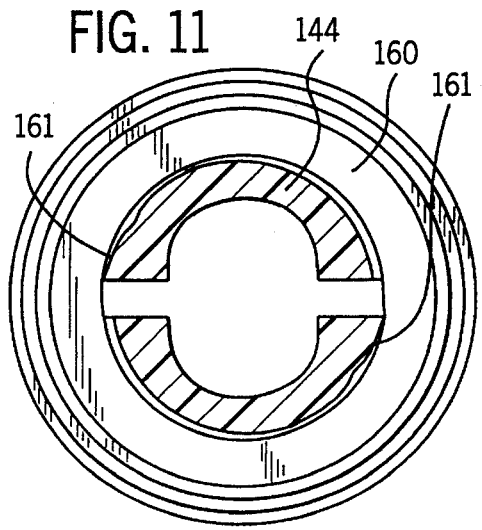

SECURABLE COLLAR FOR FLUID CONNECTOR

This application is a continuation in part of application Ser. No. 08/129,233, filed Sep. 29, 1993, (now abandoned) which is a continuation in part of Ser. No. 08/036,005, filed on Mar. 23, 1993 (now abandoned).

BACKGROUND OF THE INVENTION

The present invention relates to a securable collar which can be used to prevent the unintentional disengagement of two medical tubing connectors in fluid flow communication. More particularly, the invention relates to a collar securable by a sliding locking ring for securing a cannula-type connector to a septum-type connector during intravenous fluid administration.

In general, intravenous fluid administration to a patient involves the gravity or pump-assisted flow of a medical solution from a sterile source container through a sterile IV tubing set to a patient's vein. Usually at least one sterile connection must be made and maintained to effectively and safely transfer the medical solution from the container to the patient. A sterile connection with an intravenous tubing set can be made in a variety of ways. The traditional and most commonly used fluid flow connection is made using a sharp needle associated with the first connector to pierce a resealable elastomeric septum of a second connector. Recently, due to the concerns about accidental needle sticks, a blunt cannula connector such as the LifeShield® Blunt Cannula sold by Abbott Laboratories, rather than the traditional sharp needle connector is being used. The blunt cannula connector is used with a prepierced or partially pierced elastomeric septum connector, such as the LifeShield® Pre-pierced Reseal, also sold by Abbott Laboratories.

A primary concern with any medical tubing connector is the accidental or unintentional disengagement of the connectors. A sharp or blunt cannula can accidentally be pulled out of a reseal. An accidental disconnection can contaminate the cannula of the connector and/or allow the medical solution to spill or drain. In addition to the interruption in the intravenous therapy, accidental disconnection may compromise the sterility and integrity of the IV flow system. Contaminants may be introduced into the IV flow system if the connectors are reconnected without effective disinfecting.

The above concerns have led to medical guidelines and procedures that suggest and sometimes require that IV tubing connections be secured together. A variety of known devices are currently used for securing IV tubing connections. However, many of the known securing apparatus are undesirable, for example, because of their bulk, complexity and/or expense. Furthermore, there are other concerns such as patient discomfort, the amount of time and manipulation required front the health care provider to attach and release the securing apparatus, or the lack of effectiveness in preventing disconnections.

Tape is often used in addition to or when no suitable securing apparatus is available. However, tape has an inherent drawback when the connectors need to be quickly disconnected. Also, tape is awkward to use when one of the connectors is in close proximity to the patient's body such as the connector at the vein access site. Excessive movement of the connector at the vein access site, for example, can cause patient discomfort or damage to the vein wall.

Thus, there is a need for a simple, inexpensive, yet reliable securing apparatus that can reduce accidental disengagement of IV tubing connectors. It is desirable that the securing apparatus be readily engageable and disengageable. Further, it is desirable that the securing apparatus be easy to manipulate and compatible with different embodiments of fluid flow connectors. Finally, it is desirable that the securing apparatus be usable with blunt cannula or sharp needle connectors.

SUMMARY OF THE INVENTION

Therefore, it is a primary object of this invention to provide a simple and reliable construction for a securing apparatus used in combination with intravenous fluid flow connectors.

It is another object of this invention to provide a securing apparatus for use with intravenous tubing connectors such as either a sharp needle or a blunt cannula and their respective resealable and prepierced septums.

It is a further object of this invention to provide a securing apparatus that is easy to manipulate by the health care provider, yet reliable in securing the connectors of the intravenous tubing set.

The present invention relates to a securing apparatus for a tubing connector which secures the cannula of one connector to the reseal septum of a second connector. The first tubing connector is of the type having an axially extending hub and a cannula coaxially extending from the hub. The securing apparatus includes a radial flange circumferentially extending from the connector hub. A generally cylindrical collar includes a first collar portion circumferentially extending from the radial flange and a second collar portion further extending from the first portion. The first collar portion has a maximum outer diameter and the second collar portion has a minimum outer diameter which is larger than the maximum outer diameter of the first portion. The collar has two longitudinal notches extending the length of the collar for dividing the collar into two longitudinal semi-cylindrical segments. An annular locking ring is slidable on the collar from the first portion to the second portion. The second portion of the collar and the locking ring are constructed and arranged such that the annular locking ring forces the outer diameter of the second larger diameter portion of the collar radially inward as the locking ring moves front the first portion to the second portion.

In the preferred embodiment, the minimum outside diameter of the second portion is larger than the inside diameter of the locking ring. Thus the ring forces the longitudinal segments radially inward as the annular locking ring is slid to the second portion. A transition portion on the collar is constructed between the first and second portions to allow the annular locking ring to slide from the first to the second position. The transition portion also includes a ring retaining structure that has a slightly larger outer dimension than the outer diameter of both the first and second portions. The restraining structure preferably is at least one outward projection inclined front both the first and second portions and positioned adjacent each of the longitudinal notches. Preferably, there are two separate opposed outward projections, each having a small circumferential length.

The securing collar also includes structure for limiting rotation of the annular locking ring relative to the tubing connector when the annular locking ring is positioned on the first portion, as for example, when the connector is initially attached to the IV tubing set. Preferably this rotation limiting structure is a raised longitudinal tab on the outer surface of the first portion and a mating slot on an inner surface of the annular locking ring.

The second portion of the collar also has an inward lip on a distal end of the inner surface of the collar for engaging the radial shoulder on the second connector when the segments are forced radially inward by the annular locking ring.

In a preferred embodiment, the securing apparatus of the present invention is manufactured as an integral collar with the cannula connector.

In another embodiment, the securing apparatus is manufactured separately and can be added later to an individual cannula connector, either in the assembly plant or by retrofit in the hospital, for example.

Generally, either of the above construction allows the securing apparatus to secure the first flow connector to the second flow connector and restrain the cannula of the first connector from being inadvertently pulled from the reseal septum of the second connector.

Other features and advantages of the present invention will become readily apparent from the following detailed description, the accompanying drawings, and the appended claims.

BRIEF DESCRIPTION OF THE DRAWINGS

FIG. 8 is a cross section of the preferred embodiment of the securable collar connector assembly of FIG. 7 having the cannula engaged in fluid flow communication with the septum and the securable collar unsecured to the septum conduit;

FIG. 9 is a cross section of the preferred embodiment of the securable collar connector assembly of FIG. 7 having the cannula engaged in fluid flow communication and the securable collar secured to the septum conduit;

FIG. 10 is a schematic sectional view of the annular locking ring and the uncompressed collar along line 10—10 of FIG. 8 in the unsecured position;

FIG. 11 is a schematic sectional view of the annular locking ring and the compressed collar along line 11—11 of FIG. 9 in the secured position;

DESCRIPTION OF THE PREFERRED EMBODIMENT

Figure 1:
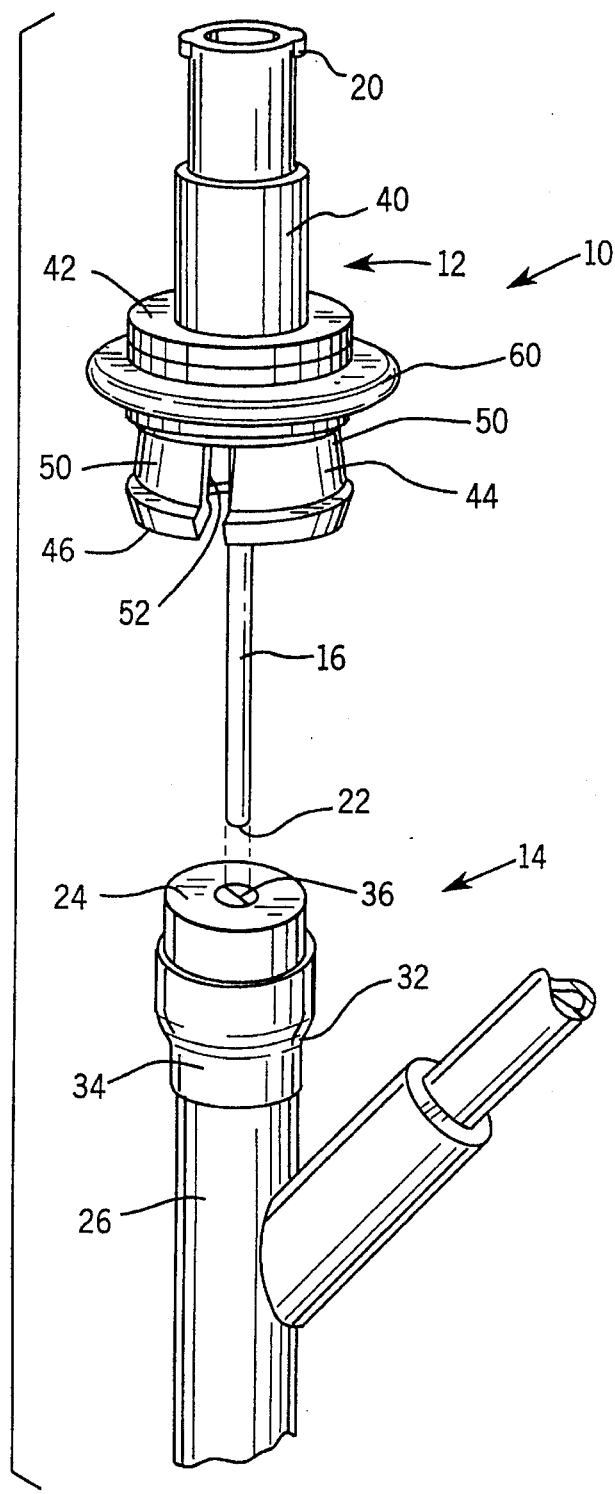
FIG. 1 is a perspective view of a blunt cannula fluid connector assembly with a separate securable collar according to a first embodiment of the present invention for connection with an associated tubular conduit having a septum at the terminal end.

Referring now to FIG. 1, a first fluid flow connector 12 is axially connectable with a second fluid flow connector 14. The first connector 12 is a male connector such as a LifeShield® Blunt Cannula and the second connector 14 is a female connector such as a LifeShield Prepierced Reseal Y-Site, both of which are sold by Abbott Laboratories. A separately manufactured securable collar 10 according to a first embodiment of the present invention is associated with the first connector 12.

The first connector 12 includes a cannula 16 which is preferably made of stainless steel. The cannula is coaxially secured in a molded plastic cannula hub 18 by adhesive or other known securing techniques. A luer fitment 20 at the upstream end of the cannula connector 12 permits the connector to be connected to a standard IV tubing set. The delivery end 22 of the cannula 16 preferably is blunt, as shown in FIG. 1.

Figure 2:
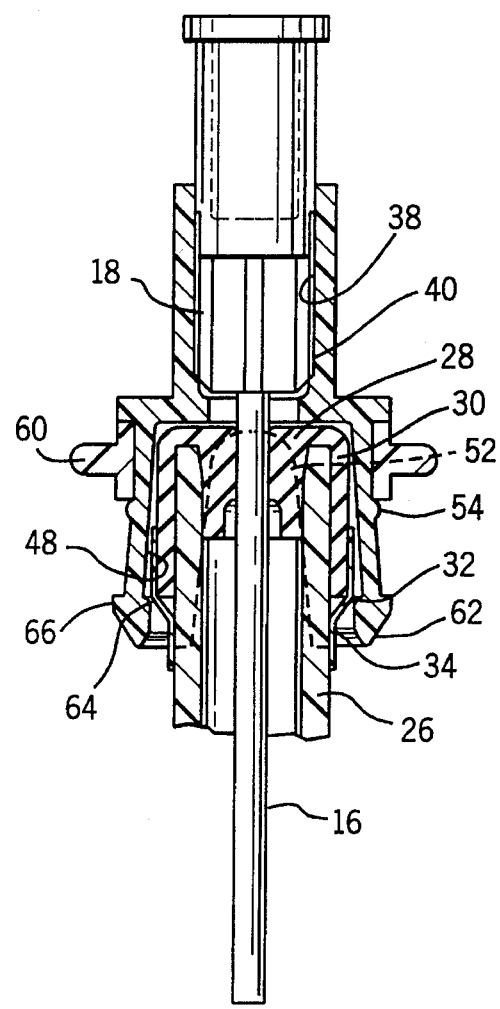
FIG. 2 is a cross-section of the connectors of FIG. 1 with the cannula connector engaged in fluid flow communication with the septum and with the securable collar according to the present invention in the unsecured position.
Figure 3:
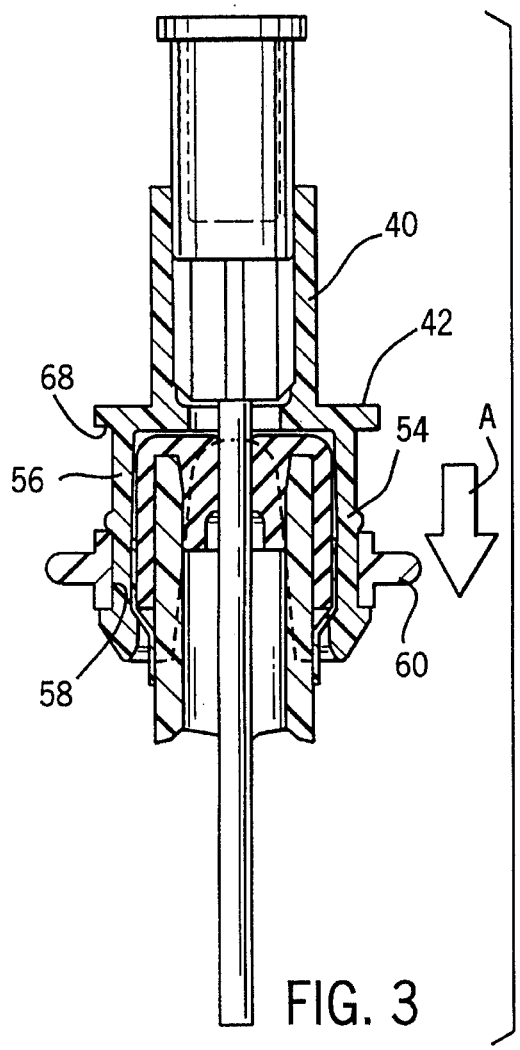
FIG. 3 is a cross-section of the engaged connectors similar to FIG. 2 with the securable collar of the present invention in the secured position.

Referring now also to FIGS. 2 and 3, the second connector 14 includes a resealable elastomeric septum 24 engagable in fluid flow communication by the cannula 16 of the first connector 12. The septum connector includes a tubular conduit such as rigid plastic housing 26 for containing the elastomeric reseal 24. As shown in the cross section of FIGS. 2 and 3, the reseal 24 includes a plug portion 28 that is inserted into the interior of the rigid tubular conduit 26 and an exterior rolled-over portion 30 which is folded down on the outside of the rigid tubular housing 26. The exterior rolled-over portion of the reseal forms a radially raised annular shoulder 32 on the outer surface of the tubular conduit 26. Typically a shrink band 34 is provided over the juncture of the rolled-over portion 30 of the reseal and the tubular conduit 26. Alternatively, the second connector 14 may have a radial shoulder integrally formed (not shown) on the exterior surface of the tubular conduit 26.

The reseal 24 is preferably manufactured of an elastomeric material such as a medical grade latex rubber or synthetic elastomeric material that can be sterilized. The septum may be manufactured with an unpierced diaphragm portion (not shown) that is pierceable by a sharp cannula. Preferably, the septum has a prepierced diaphragm portion 36, such as the previously mentioned LifeShield Prepierced Reseal sold by Abbott Laboratories for use with a blunt cannula.

The securing apparatus 10 of the first embodiment of the invention includes a separately manufactured collar housing 40. The housing 40 has a bore 38 for receiving the hub 18 of the first connector 12 with a press or interference fit. A generally radially extending deflectable flange 42 extends from the housing 40. A generally cylindrical and preferably frustum-shaped collar 44 extends longitudinally forward from the radial flange 42. The collar is coaxial with the cannula 16 and oppositely extending from the tubular housing 40.

At least part of the outer surface of the collar 44 is outwardly spreading in the axially forward direction. As seen in the cross-section of FIG. 2, the hollow collar of the first embodiment has a continuous frustum-shape that is outwardly expanding (i.e., splayed) in the axially forward direction. The collar 44 extends longitudinally forward from the flange 42 and has an open end 46 and hollow bore 48 for receiving the terminal end of the septum conduit.

The outer surface of the collar has a first collar portion 56 adjacent the flange 42 and a second collar portion 58 between the first portion and the open end. The first collar portion 56 of the first embodiment of the invention in FIG. 2 is frustum-shaped and is continuous with the frustum shape of the second collar portion 58. Thus, the first frustum-shaped portion 56 is characterized by a first range of increasing diameters including a first maximum diameter. The second frustum-shaped portion 58 is characterized by a second range of increasing diameters including a second minimum diameter. The diameters of the second portion are larger than the diameters of the first portion.

The frustum-shaped collar includes two longitudinally extending notches 52 which extend substantially the full length of the collar and divide the collar into two longitudinal collar segments 50. As shown in FIG. 1, for example, two diametrically opposite notches 52 divide the collar 44 into two longitudinal semi-cylindrical collar segments 50. For manufacturing and functional purposes, two opposed notches and semi-cylindrical segments are desirable.

The tubular collar 44 includes a transition portion 54 (as seen in FIGS. 2 and 3) that divides the frustum-shaped collar 44 into a first (or proximal) portion 56 and a second (or distal) portion 58. The first frustum-shaped portion 56 circumferentially extends from the radial flange 42. The second portion 58 further extends from the first portion 56. The transition portion 54 may include a small annular slightly outward projection (shown) or a discrete bump having a small radial length (described later) located approximately midway on the outer surface of the frustum-shaped collar 44, as shown in FIGS. 2 and 3, for example.

Referring again to FIGS. 1–3, an annular locking ring 60 circumscribes and is slidable along the outer surface of the frustum-shaped collar 44 front the first portion 56 to the second portion 58. The ring has an inner diameter that is smaller than the minimum diameter of the outer surface of the second portion 58. When the first connector 12 is engaged with the second connector 14 and the annular locking ring 60 is positioned on the first portion 56 as shown in FIG. 2, the inner surface of the longitudinal segments 50 of the second portion 58 of the collar have sufficient radial clearance to receive the radial shoulder 32 on the second connector 14 within the inner bore of the collar. However, when the annular locking ring 60 is advanced past the transition portion 54 to a position over the second portion 58 of the collar, as shown by arrow A in FIG. 3, the ring 60 compresses the outer surface of the second portion 58 to resiliently pivot the two longitudinal segments 50 radially inward along the deflectable flange 42 so that the inner surface of the open end of the collar engages the radial shoulder 32 of the tubular conduit 14.

The collar 44 preferably has an inward extending lip 64 at the distal or open end 46 of the inner surface, so that the lip can engage the raised shoulder 32 on the septum connector. The collar also preferably includes an external lip 66 on the outer surface at the open end 46 to prevent the annular locking ring 60 front sliding completely off the collar segments 50 when the annular locking ring 60 is advanced to the secured (or locked) position. A radially outward extending structure, such as an extension 68 of the flange 42 at the closed end of the collar prevents annular locking ring 60 from being pulled completely off the collar when the annular locking ring 60 is retracted to the unsecured (or unlocked) position.

The slight outward projection at the transition portion 54 on the collar 44 keeps the annular locking ring 60 in the unsecured position until sufficient force is applied to the annular locking ring 60 to cause the ring to move over the transition portion 54. The tapered lead-in 62 on the forward part of the external lip 66 at the open end of the collar assists in the initial assembly of the annular locking ring 60 to the securing collar 10.

The manual manipulation required by the healthcare worker to slide the annular locking ring 60 over the outward projection at 54 to the forward secured position is simply a continuation of the axial motion required to engage the connectors 12 and 14 together. Thus, the securable collar 10 of the present invention is easily and readily secured. When the ring 60 is secured in the second position by the outward projection of the transition portion 54, the secured collar 44 provides enough axial resistance so that the cannula connector 12 cannot be unintentionally withdrawn from the septum connector 14.

Figure 4:
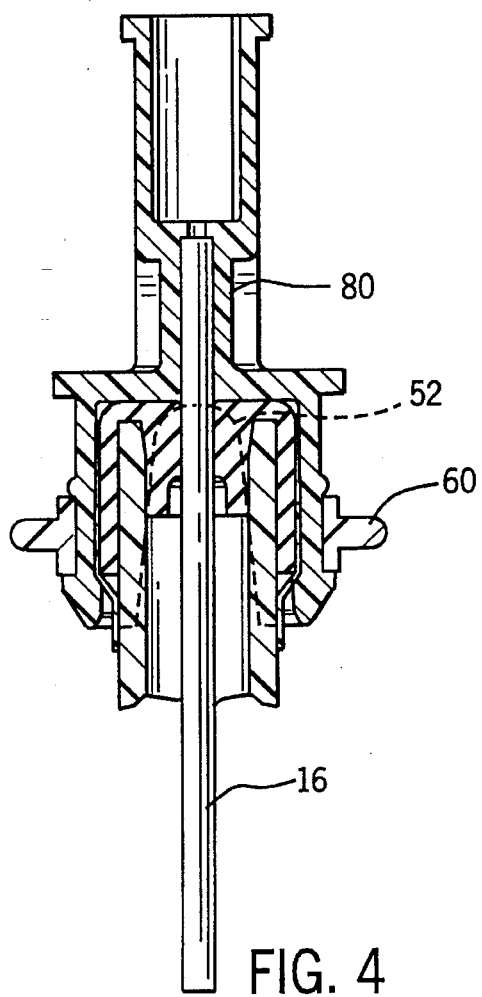
FIG. 4 is a cross-section of an alternative embodiment of the present invention wherein the securable collar is integrally formed with a cannula connector.

FIG. 4 shows a second embodiment of the invention having a one-piece integrally molded connector hub and collar housing 80. The cannula 16 is insert molded or bonded in the integral hub and collar housing 80 during manufacture. Thus the integral connector and collar device requires no further assembly other than to assemble the annular locking ring 60 on the tubular collar 44.

Figure 5:
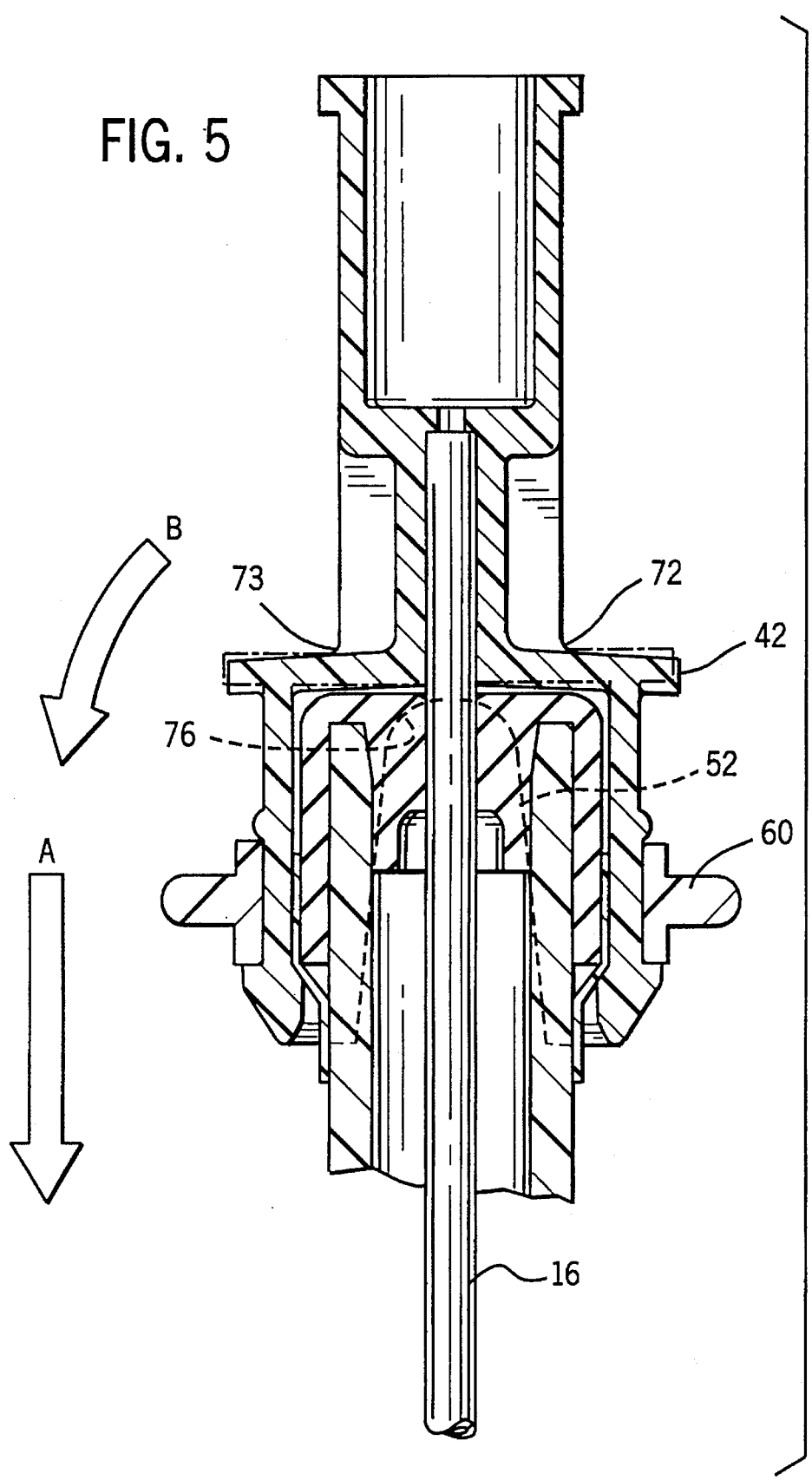
FIG. 5 is an enlarged view of FIG. 4 showing the deflection of the radially extending flange in the secured position.

FIG. 5 is an enlarged view of FIG. 4 and shows the second integral connector and collar embodiment of the present invention. The collar has two diametrically opposite notches 52 (shown in phantom) forming two longitudinal collar segments 50. The notches extend the full length of the collar to a notch closed end 76 adjacent the radial flange 42 so as to divide the collar into two longitudinal semi-cylindrical segments. Because of the split collar structure, the two longitudinal collar segments pivot radially inward along the resiliently deflectable flange 42 at a flange portion located generally between points 72 and 73 on the radial flange. The portion of the radial flange that deflects to cause the pivoting is parallel to the longitudinal plane bisecting the two opposed notches 52 in the collar 44. Thus, according to this invention, the two collar segments 50 of the tubular collar 44 remain substantially straight and pivot radially inward only at the radially extending flange 42. The semi-cylindrical cross-sectional shape of the two collar segments 50 structurally resists deflection along the longitudinal length of the segments so that only resiliently deflectable pivoting occurs at the deflectable radial flange 42.

For other than two diametrically opposite recesses and/or semi-cylindrical segments, some deflection is likely to occur on the collar, resulting in a radially inward bending of the segments rather than a deflection of the radially extending flange.

Figure 6:
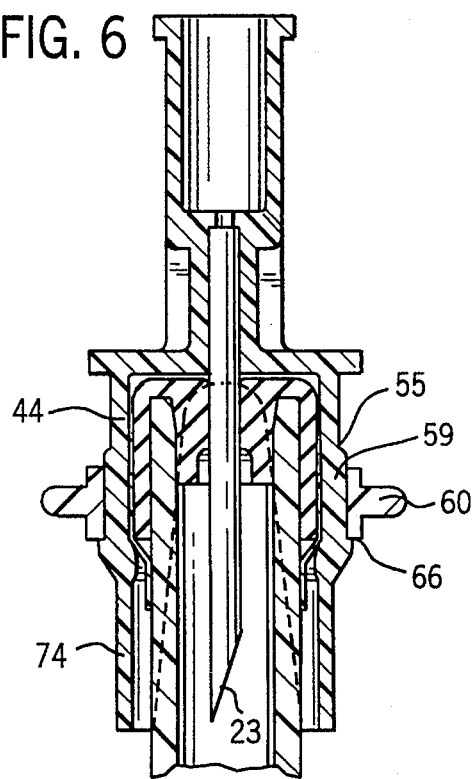
FIG. 6 is a cross-section similar to FIG. 4 showing another alternate embodiment of the present invention including a shroud portion extending concentrically beyond the end of a sharp cannula.

As illustrated in FIG. 6, a third embodiment of the invention is shown having a sharp cannula connector 23 that is wholly contained within a protective shroud 74 extending from the tubular collar 44 so as to prevent accidental needle stick. Thus the tubular collar 44 and the protective shroud portion 74 function together as a securing apparatus and a needle protecting apparatus.

Also as shown in FIG. 6, an integral radial shoulder 55 is formed on the collar 44. The larger diameter of the second (or distal) portion of the collar 44 is due to a thicker (i.e., built-up) collar dimension 59 at the second portion. In addition to the outward frustum-shape of the second portion or as an alternative to the outward frustum-shape, the additional thickness of the second portion on a cylindrical collar by itself makes the outer diameter of the second portion larger than the outer diameter of the first portion. The thicker dimensioned collar of the second portion causes the annular locking ring to compress the second portion 58 radially inward. The ring compresses the thickened second portion and pivots the longitudinal segments radially inward at the radial flange 42 to engage the second connector 14 in the same manner as the ring compresses the previously described outward splayed frusto-conical collar. Thus, a ring slidable on any combination of a frustum-shaped collar and/or a thicker (i.e., built-up) dimension at the second portion of the collar will cause the longitudinal segments to pivot radially inward from the radial flange.

Figure 7:
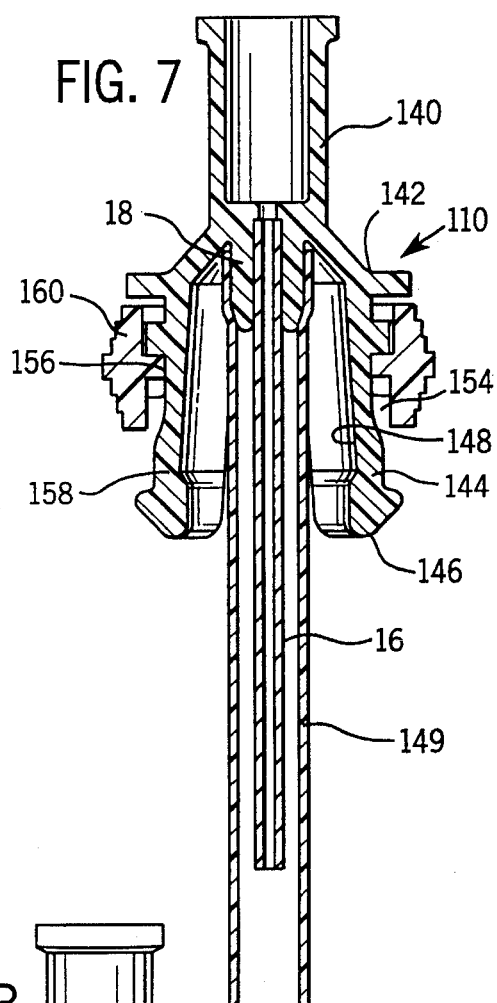
FIG. 7 is a cross section of the preferred embodiment of the present invention including a securable collar integrally formed with a blunt cannula connector.

A preferred embodiment of the present invention is shown in FIG. 7. A fluid connector integrally manufactured with a securable collar 110 has a body 140 including an extending cannula 16. The connector body includes a deflectable annular flange 142 extending generally radially from the body.

A hollow generally frustum-shaped collar 144 extends from the flange 142 to an open end 146. The collar has an inner surface defining a bore 148 for receiving the terminal end of a tubular conduit. The collar has an outside surface including a first collar portion 156 adjacent the flange and a second collar portion 158 between the first portion and the open end. The outside surface of the first portion 156 is substantially cylindrical and has a first maximum diameter which is the diameter of the outer cylindrical surface. The second portion is preferably frustum-shaped and has a range of increasing diameters. The diameters increase from a second minimum diameter which is larger than the first maximum diameter (i.e., the diameter of the cylindrical portion).

The collar has two diametrically opposed longitudinal notches 152 extending from the open end 146 and through the first and second portions so as to divide the collar into two longitudinal semi-cylindrical segments 150.

The collar 144 also includes a ring 160 circumscribing and slidable along the outer surface of the collar from a first position on the first portion to a second position on the second portion. The ring has an inner diameter which is smaller than the minimum diameter of the second portion so as to compress the outer surface of the second portion radially inward when the ring is in the second position.

Referring now to FIGS. 8 and 9, when the annular locking ring 160 is slid from the first portion 156 in FIG. 8 to the second portion 158 in FIG. 9, the annular locking ring 160 compresses the outer surface of the second portion 158 to resiliently pivot the two longitudinal segments 150 radially inward along the deflectable radial flange 142. Thus, the inner surface at the open end 146 of the collar moves radially inward to capture the radial shoulder 32 of the tubular conduit 14.

As shown in FIGS. 7–9, the inner surface of the second portion 158 of the collar also has an inward lip 164 at the open end 146 for engaging the radial shoulder of the second connector 14 when the segments 150 are forced radially inward by the annular locking ring 160 as best seen in FIG. 9.

As previously discussed, the semi-cylindrical cross-sectional shape of the segments 150 helps the longitudinal segments remain substantially straight without deflecting along the longitudinal length. Thus, the resilient deflection of the collar takes place at radial flange 142 and not along the longitudinal segments 150 of the collar.

Figure 7A:
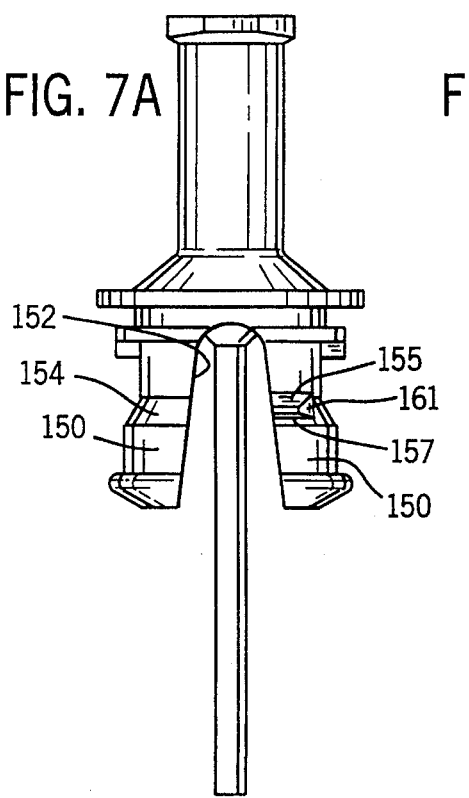
FIG. 7A is a side view of the preferred embodiment of FIG. 7 with the locking ring removed.
Figure 7B:
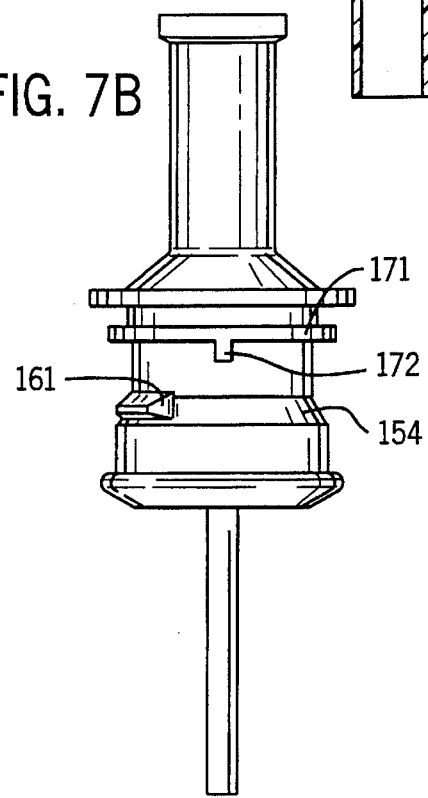
FIG. 7B is another side view of FIG. 7A rotated 90°.

As shown in FIGS. 7A and 7B, a transition portion 154 of the securable collar 110 is constructed between the first and second portions. The transition portion 154 also includes structural means to retain the annular locking ring 160 in the first and second positions. The transition portion 154 includes at least one slightly outward projection 161. The projection includes an inclined ramp 155 on the proximal side of the outward projection to assist the annular locking ring 160 in moving over the transition portion 154 to the second position on the larger diameter portion 158. The outward projection 161 also includes an outwardly inclined ramp 157 on the distal side of the projection to assist the ring in moving from the second portion 158 back to the first portion 156. As seen in FIGS. 10 and 11, the transition portion 154 preferably includes two discrete projections 161, each longitudinally positioned near the midpoint of one of the two separate segments 150 of tubular collar 144. Each projection 161 has a small circumferential length and is radially located immediately adjacent one of the two longitudinal notches 152.

The securing collar 110 also advantageous includes structure for limiting rotation of the annular locking ring 160 relative to the tubular housing 140 of the connector 12. The rotation limiting structure allows torque to be transmitted from the ring to the housing body when the annular locking ring 160 is positioned on the first portion 156. For example, in FIG. 12, when the integral connector 110 is initially attached to the IV tubing set 170 by a threaded luer fitment, and in FIG. 13 when the connector is later detached, it is desirable that the annular locking ring 160 not rotate relative to the tubular housing 140. Preferably the rotation limiting structure is a raised longitudinal tab 172 on an outer surface of the first portion 156 (best seen in FIG. 7B) and a mating slot 174 on an inner surface of the annular locking ring 160 as shown in FIG. 8 that can be axially engaged (by slight force in the direction of arrow F) to prevent rotation of the ring 160 relative to connector body 140.

The outward annular lip 171 associated with the raised tab 172 retains the annular locking ring 160 on the first portion 156. Likewise external lip 166 on the outer surface at the open end of the collar retains the annular locking ring 160 on the second portion 158.

The preferred embodiment of the securable connector apparatus according to the present invention is readily manufactured by an injection molding process using a resilient plastic. The preferred material for the securable collar and connector is polypropylene or polyethylene. These materials are readily injection molded. The collar is preferably manufactured integral with the connector 12 as described in the preferred embodiment of FIG. 7. The securable collar can also be manufactured separately and retrofitted with separate connectors as described in the first embodiment of FIG. 1. The connector can be molded with the metal cannula 16 in place or the metal cannula can be added later to a molded connector.

Figure 12:
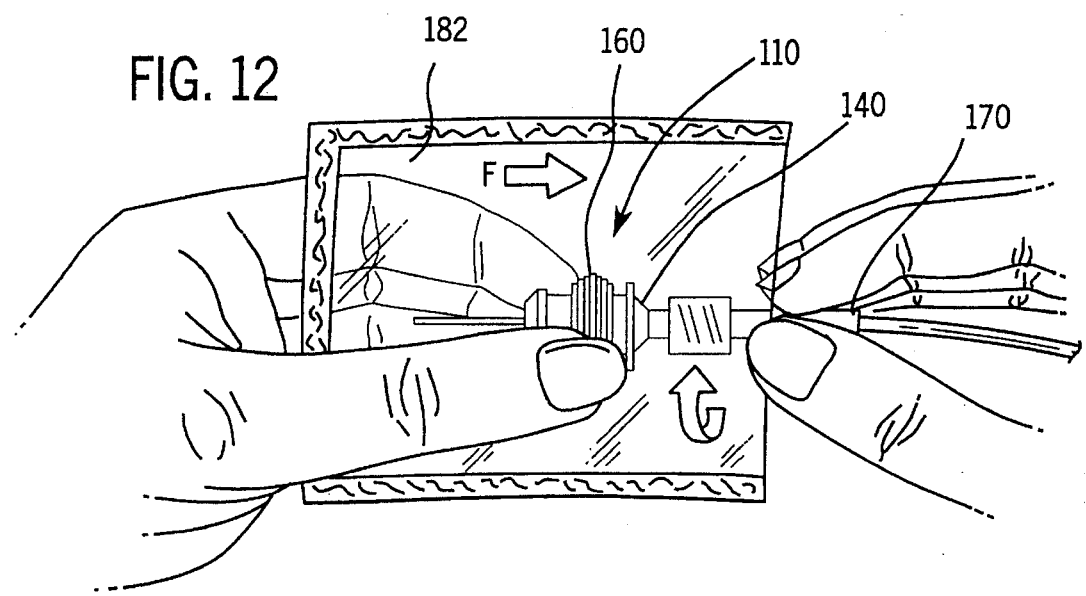
FIG. 12 is a schematic depiction of the cannula connector and securable collar of the present invention during an initial connection of the connector to an IV tubing set.
Figure 13:
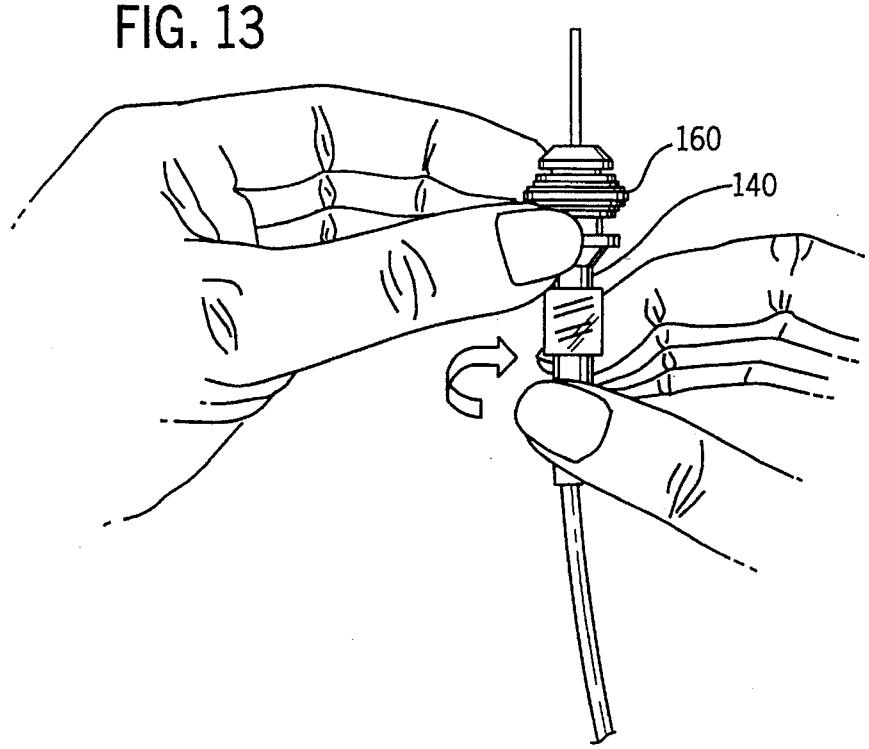
FIG. 13 is a schematic depiction of the cannula connector and securable collar of the present invention during disconnection of the connector from the IV robing set.

The assembled integral connector and securable collar 110 of the preferred embodiment is sterilized and packaged in a conventional manner, for example as shown in FIG. 12.

The preferred embodiment of the present invention with reference to FIGS. 7–12 is advantageously used in the following manner. The connector assembly is attached to tubing set 170 and the sheath 149 is removed from the hub. The cannula 16 of the connector assembly is inserted into the reseal septum 14. The securable collar 110 is pushed axially forward so that the open end of the collar 144 encloses the terminal end of the conduit and covers the annular shoulder portion 32 on the second connector 14. The annular locking ring 160 is then slid forward on the collar 144 over the transition portion 154 and outward projections 161 to the second position to force the longitudinal segments 150 to pivot radially inward from the radial flange 142. The outward projections 161 restrain the locking ring in the second position to secure the engagement of the inward lip 164 around the radial shoulder of the conduit. The collar thus secures the first connector 110 to the second connector 14 to reduce accidental disconnection.

With the securable collar according to the present invention, the axial force necessary to disengage the integral connector 110 from the septum connector 14 is increased. Previously, without any securing collar only a small resistance force due to the frictional contact between the metal canula and the elastomeric septum prevented accidental disconnection. The threshold axial force necessary to cause disconnection for the present invention is increased due to the mechanical force necessary to above the locking ring over the outward projections 161 at the transition portion 154. The new threshold disconnecting force is sufficient to resist most accidental disconnection situations.

While several embodiments of the invention have been described, modifications within the scope of the present invention will be readily apparent to one of ordinary skill in the art. For example, the securing collar of the present invention may be used with any of the known fluid flow connectors such as sharp needles and unpierced reseals or blunt cannula and prepierced reseals although the preferred connector shown in the disclosed embodiments are primarily disclosed with respect to blunt cannula and prepierced reseals. All such modifications are intended to be covered by scope of the accompanying claims.

What is claimed:

1. A fluid connector assembly for securably connecting to a tubular conduit having a septum at a terminal end and a radial shoulder proximate the septum, the connector assembly comprising:

a connector body having an axially extending cannula for insertion into the septum;

a generally radially extending, resiliently deflectable flange extending from the connector body;

a hollow generally cylindrical collar extending longitudinally from the flange and coaxially with the cannula to an open end;

the hollow collar having an inner surface defining a bore for receiving the terminal end of the tubular conduit and a radially inward extending lip on the inner surface of the collar at the open end of the collar;

the collar having an outer surface including a first portion adjacent the flange having a first maximum diameter and a second portion between the first portion and the open end of the collar having a second minimum diameter which is larger than the first maximum diameter;

the collar having two diametrically opposed notches, each notch extending longitudinally from the open end of the collar through the first and second portions of the collar to a notch closed end adjacent the flange so as to divide the collar into two longitudinal semi-cylindrical segments; and a ring longitudinally slidable along the outer surface of the collar from a first position on the first portion to a second position on the second portion, the ring having an inner diameter which is smaller than the second minimum diameter of the collar and which compresses the outer surface of the second portion when the ring is slid to the second position to pivot the two longitudinal segments of the collar radially inward at the deflectable flange so that the inward lip at the open end of the collar engages the radial shoulder of the tubular conduit.

2. The fluid connector assembly of claim 1 wherein the longitudinal segments pivot along a portion of the radial flange, the flange portion being generally parallel to a longitudinal plane which bisects both longitudinal notches.

3. The fluid connector assembly of claim 2 wherein at least the second portion of the outer surface of the collar is frustum-shaped.

4. The fluid connector assembly of claim 3 further including means on the collar for restraining the slidable ring in the first and second positions.

5. The fluid connector assembly of claim 4 wherein the restraining means includes at least one outward projection located between the first and second portions, and wherein at least one outward projection is inclined radially outward from both the first maximum diameter and second minimum diameter.

6. The fluid connector assembly of claim 5 wherein the restraining means includes two outward projections, each projection on a separate one of the two longitudinal segments and each projection flanking a separate one of the two longitudinal notches.

7. The fluid connector assembly of claim 4 further including means for limiting the relative rotation of the sliding ring on the collar in the first position.

8. The fluid connector assembly of claim 7, further including a raised tab on the outer surface of said first portion of the collar wherein the rotation limiting means is a slot on the slidable ring constructed and arranged to axially register in said raised tab.

9. The fluid connector assembly of claim 4 wherein at least a first portion of the inner surface of the collar adjacent the open end of the collar is frustum-shaped.

10. The fluid connector assembly of claim 9 further including a radially outward extending shoulder on the outer surface of the second portion at the open end of the collar to prevent axial removal of the ring from the collar when the ring is in the second position.

11. The fluid connector assembly of claim 3 wherein the first portion of the outer surface of the collar is frustum-shaped.

12. The fluid connector assembly of claim 11 further including means on the collar for restraining the slidable ring in the first and second positions wherein the restraining means includes at least one outward projection located between the first and second positions, the projection inclined radially outward from both the first maximum diameter and the second minimum diameter.

13. The fluid connector assembly of claim 12 wherein the first and second portions of the outer surface of the collar is a continuous frustum.

14. The fluid connector assembly of claim 13 wherein the inner surface of the collar is frustum-shaped.

15. The fluid connector assembly of claim 14 further including a radially outward extending lip on the outer surface of the second portion at the open end of the collar to prevent axial removal of the ring from the collar when the ring is in the second position.

* * * * *